United States Patent [19]
Brown

[11] Patent Number: 5,323,765
[45] Date of Patent: Jun. 28, 1994

[54] APPARATUS AND METHOD FOR ENDOSCOPIC SURGERY

[76] Inventor: Michael G. Brown, 17270 Red Oak Dr., #190, Houston, Tex. 77090

[21] Appl. No.: 980,360

[22] Filed: Nov. 23, 1992

Related U.S. Application Data

[63] Continuation-in-part of Ser. No. 801,049, Dec. 3, 1991, abandoned.

[51] Int. Cl.$^5$ .................................................. A61B 1/00
[52] U.S. Cl. .................................. 128/4; 128/898; 606/170; 30/330
[58] Field of Search ................ 128/4, 898, 3; 606/85, 606/167, 170, 190, 176, 184, 53, 171; 604/164; 30/329, 330, 331, 337, 338, 339

[56] References Cited

U.S. PATENT DOCUMENTS

| | | |
|---|---|---|
| 2,741,248 | 4/1956 | Woodhall .......................... 606/176 |
| 3,640,280 | 2/1972 | Slanker et al. ...................... 606/84 |
| 3,845,554 | 11/1974 | Joanis et al. ...................... 30/330 X |
| 4,169,312 | 10/1979 | Mar ........................................ 30/337 |
| 4,497,320 | 2/1985 | Nicholson et al. ............. 606/170 X |
| 4,733,662 | 3/1988 | DeSatnick et al. .................. 606/171 |
| 4,777,725 | 10/1988 | Hirsch ................................... 30/331 |
| 4,962,770 | 10/1990 | Agee et al. ...................... 606/170 X |
| 4,985,035 | 1/1991 | Torre ................................. 606/84 X |
| 4,997,419 | 3/1991 | Lakatos et al. ................. 606/190 X |
| 5,029,573 | 7/1991 | Chow ..................................... 128/4 |
| 5,120,318 | 6/1992 | Nallapareddy ..................... 604/164 |

FOREIGN PATENT DOCUMENTS 517608 12/1992 European Pat. Off. .............. 128/20

Primary Examiner—Richard J. Apley
Assistant Examiner—Karen A. Jalbert
Attorney, Agent, or Firm—Browning, Bushman, Anderson & Brookhart

[57] ABSTRACT

An apparatus for endoscopic surgical treatment of carpal tunnel syndrome, heel spur syndrome, or other conditions requiring fibrous tissue division and a method for endoscopic treatment of carpal tunnel syndrome are disclosed which include a slotted cannula, an obturator for guiding the cannula into a body opening, an elevator, a retractor, and a hooked surgical knife. The elevator and retractor are used in separating tissue at a surgical opening into the wrist, hand, foot or other location and the obturator and cannula are inserted into the opening for endoscopic division of the carpal ligament, plantar fascia or other tissue. The obturator is removed and a videoarthroscope is inserted in the one end of the cannula while the knife is inserted in the other end to permit direct observation of the procedure as the ligament is divided in one step. The instruments are very small and leave only small openings which reduce the trauma and facilitate early recovery from the surgical procedure.

14 Claims, 9 Drawing Sheets

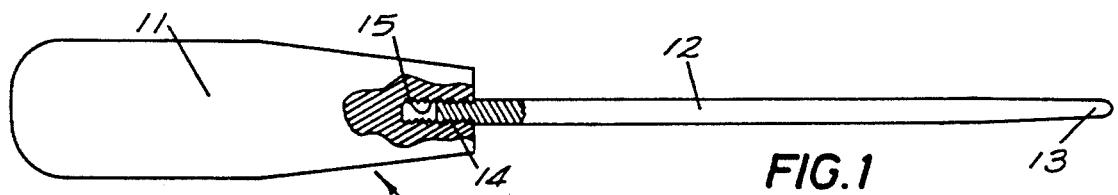
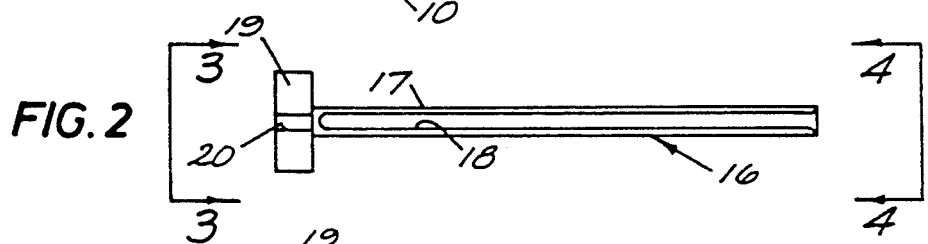
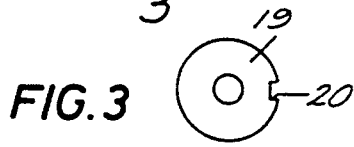
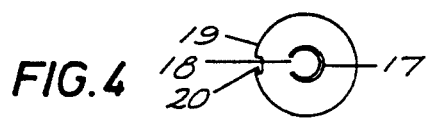
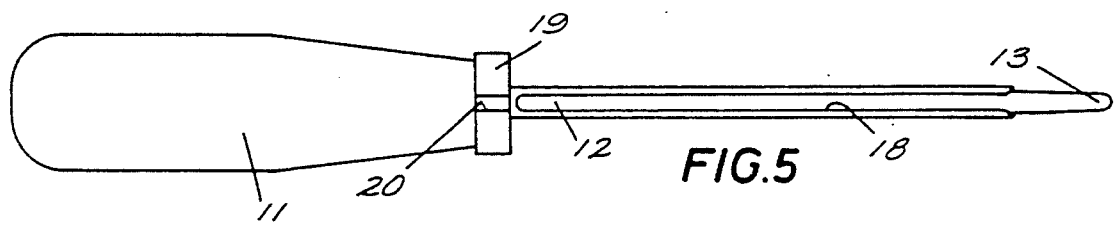
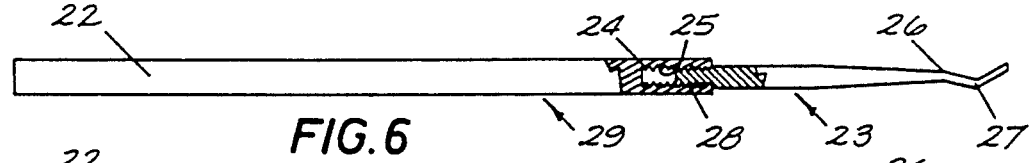
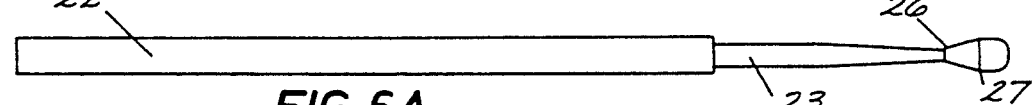
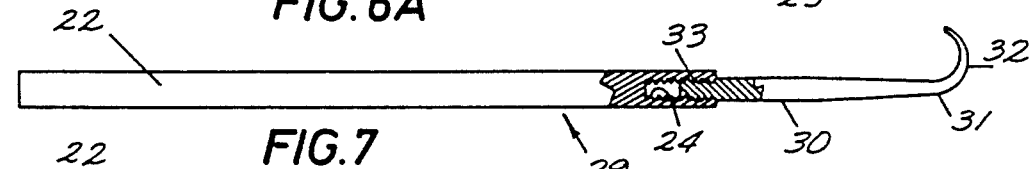
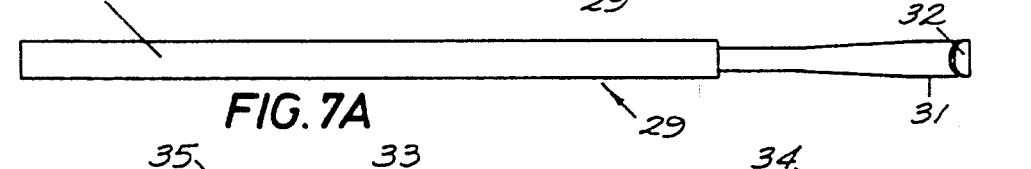

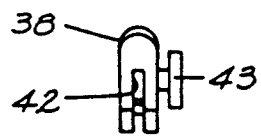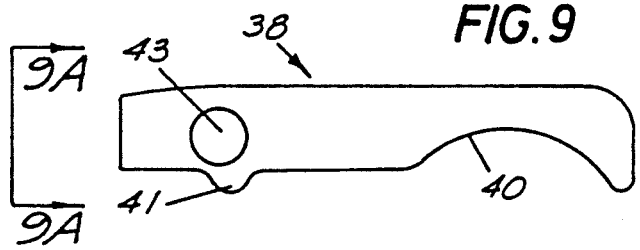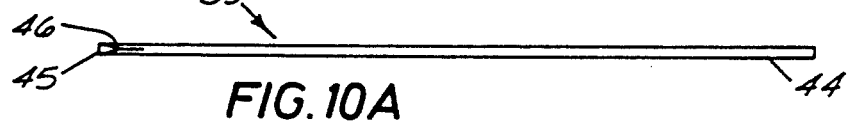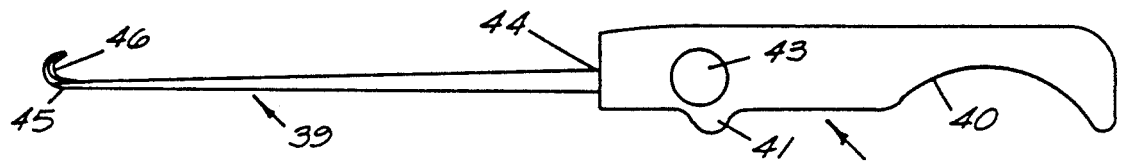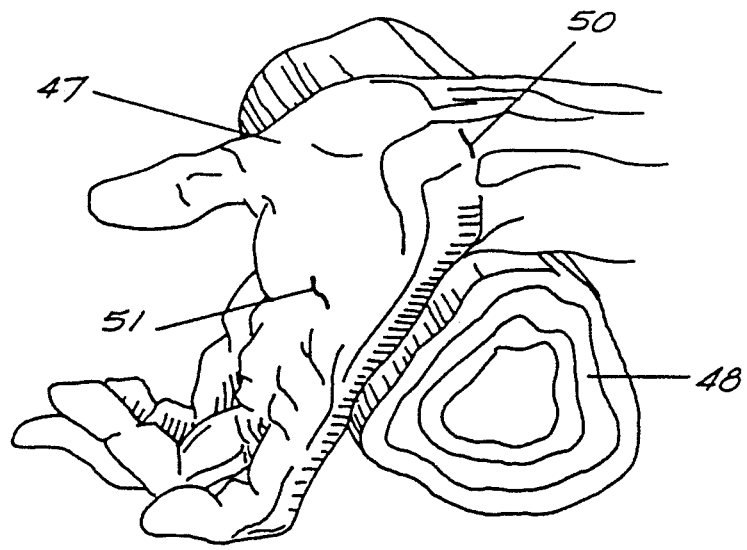

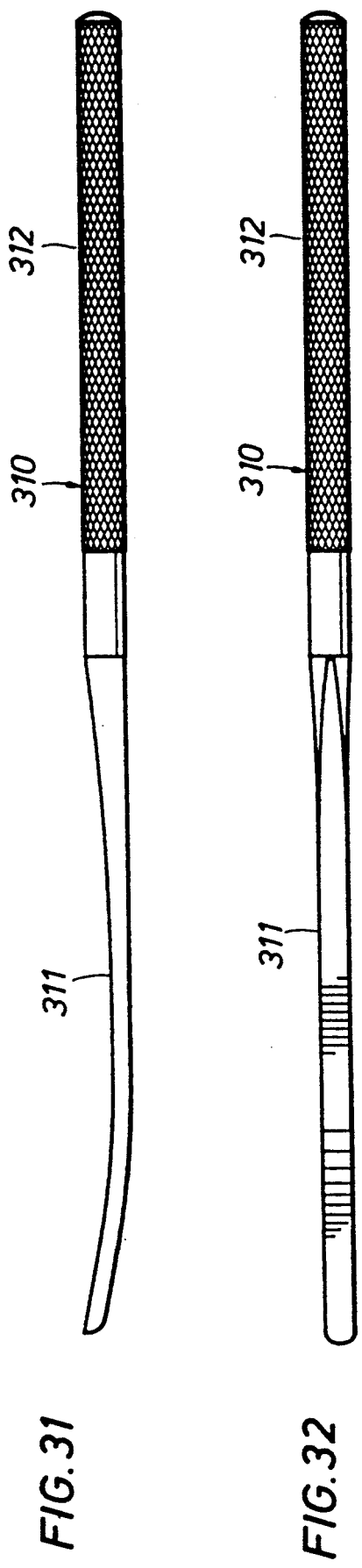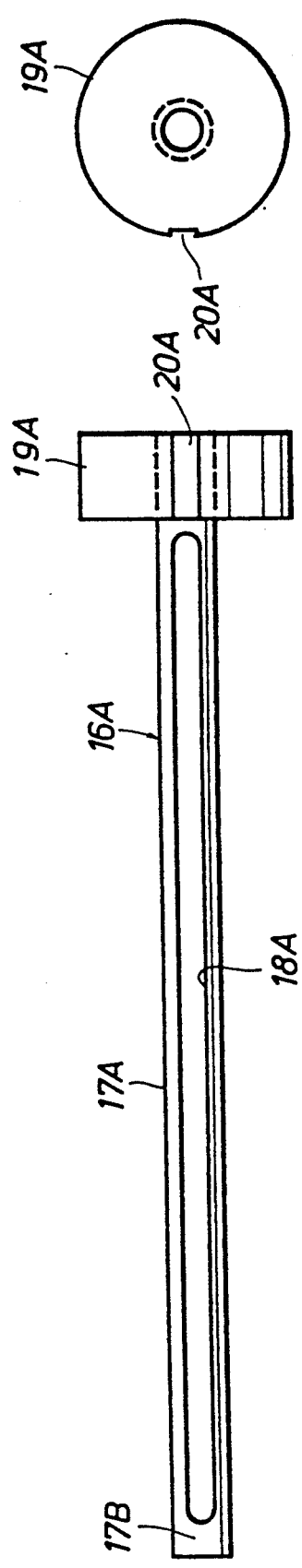
FIG.31
FIG.32
FIG.18
FIG.19

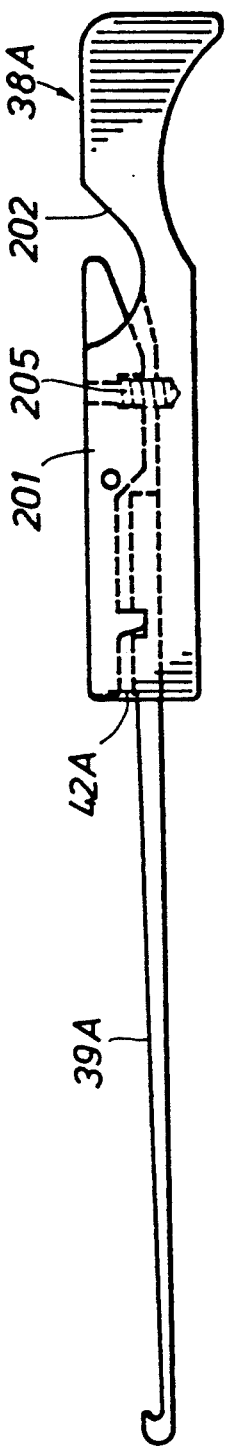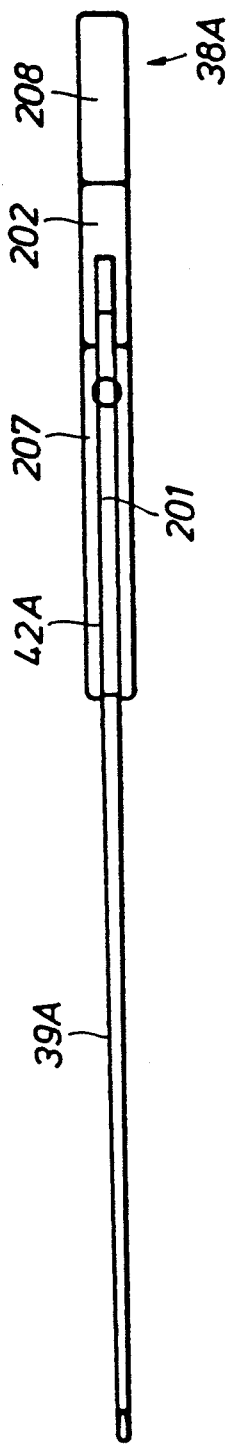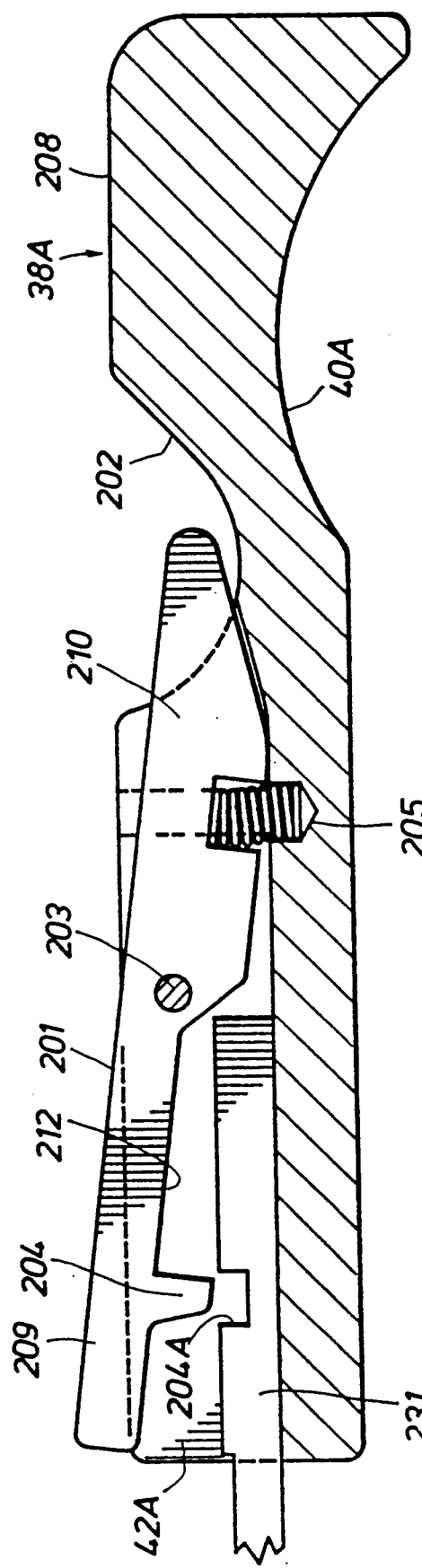

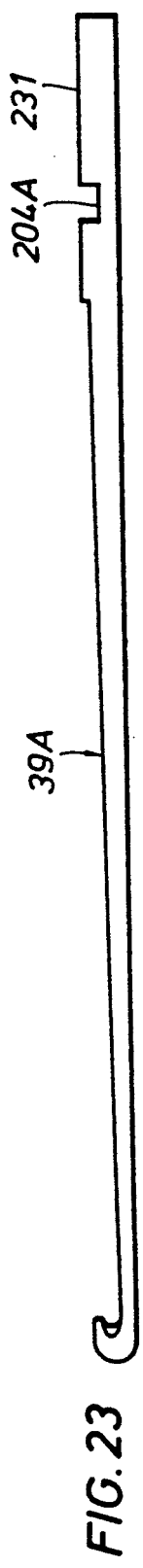
FIG. 23
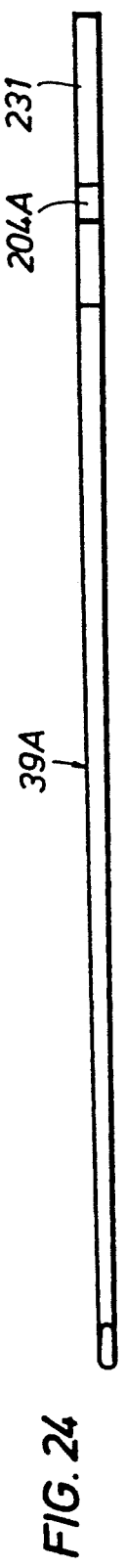
FIG. 24
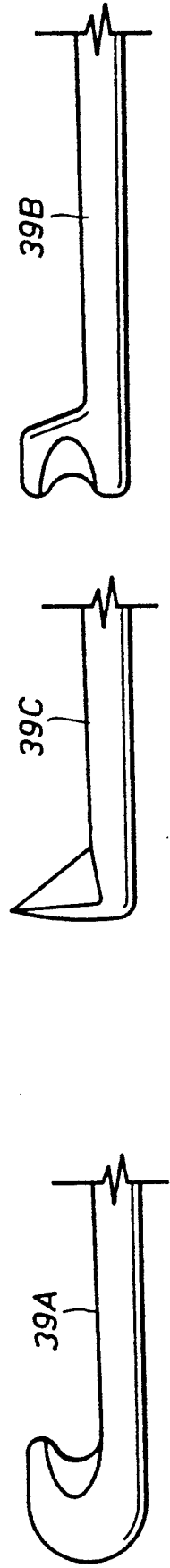
FIG. 25
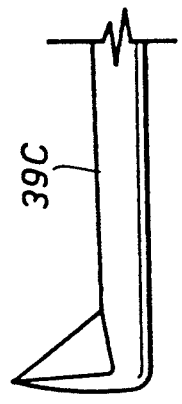
FIG. 26
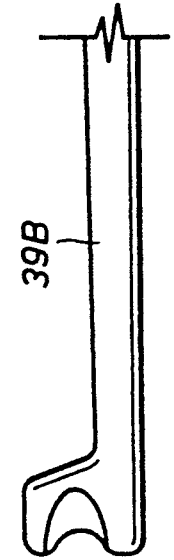
FIG. 27
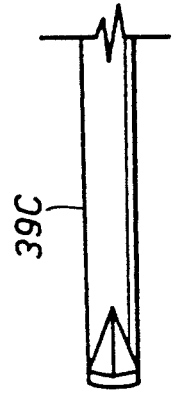
FIG. 28
FIG. 29
FIG. 30

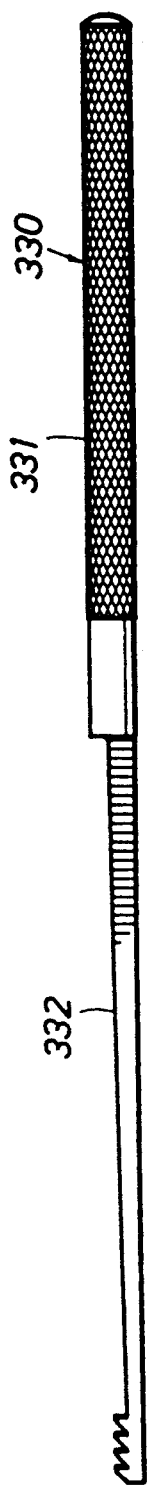
FIG. 33 FIG. 34 FIG. 35 FIG. 36 FIG. 37 FIG. 38

APPARATUS AND METHOD FOR ENDOSCOPIC SURGERY

BACKGROUND OF THE INVENTION

1. Field of the Invention

This application is a continuation in part of patent application Ser. No. 07/801,049 filed on Dec. 3, 1991, now abandoned.

This invention relates to new and improved surgical apparatus for endoscopic tissue division and an improved method for endoscopic surgery for correction of carpal tunnel syndrome. The invention relates generally to a surgical apparatus and technique utilizing a videoarthroscope and a slotted cannula and surgical knife insertable therethrough for carpal tunnel surgery and other endoscopic tissue divisions.

2. Related Art

Carpal tunnel syndrome which is caused by the compression of the median nerve within the carpal tunnel is excruciatingly painful and requires the surgical release of the transverse carpal ligament for relief. The carpal tunnel is formed by an arch of the wrist bones spanned on its palmer surface by the transverse carpal ligament. The carpal tunnel functions to provide for movement of the digital flexor tendons as they pass through the tunnel. The tendons transmit force out into the fingers and impart only an appropriate amount of tension to develop torque at the level of the wrist.

Within the carpal tunnel, the tendons are lubricated and nourished by the radial and the ulnar bursa. The median nerve also shares the carpal tunnel, then branches out to provide sensory innervation to the palmer surfaces of the thumb, index, long and a portion of the ring finger. In addition, a small motor branch of the median nerve supplies the thenat muscles which are responsible for lifting the thumb into opposition with the fingers.

Carpal tunnel syndrome encompasses various clinical signs and symptoms resulting from pressure on the median nerve inside the carpal tunnel. Typically, there is increased pressure within the carpal tunnel, which interferes with the function of the median nerve. The patient experiences numbness and tingling in the fingers, together with pain that may radiate as far as the shoulder or base of the neck. Impaired grasping ability, due to sensory deprivation from the fingers, loss of sleep from pain and numbness in the hand, and weakness or atrophy of the thenar muscles may also occur.

The pathology generally results from a swelling of the synovial membranes which is often idiopathic. Carpal tunnel syndrome can also be caused by pressure on the median nerve from rheumatoid arthritis or edema in the final trimester of pregnancy.

Many cases of carpal tunnel syndrome have been treated by cortisone or other medications being injected into the carpal tunnel. However, if symptoms persist and/or recur, or if the patient has severe sensory deficit or loss of function in the thenar muscles, then surgical decompression of the nerve by release of the transverse carpal ligament is often indicated.

Current open wrist surgical procedures require a longitudinal incision paralleling the thenar crease and extending down through the skin, subcutaneous fat, and palmer fascia to divide the palmaris brevis muscle and then the transverse carpal ligament. Although the carpal tunnel is inspected, most cases do not require any surgical treatment within the carpal tunnel, other than the division of the ligament. Thereafter, the skin is sutured and the patient is splinted for approximately three weeks. A typical surgery can be done in less than a half hour, including the dressing, and is performed as an outpatient procedure.

A patient whose occupation does not require extensive use of the hands can generally return to work within a few days, although writing may be difficult if the dominant hand is involved. However, in many cases where the syndrome is occupationally related, the patient is frequently disabled for six to eight weeks or more. If the patient is a manual laborer, two or three months may pass before a return to gainful employment. This postoperative morbidity is primarily due to persistent tenderness in the palm as the scar tissue matures. Most patients experience tenderness in the heel of their hand for four to six months following the surgery.

Another surgical technique involves the release of the tendons in the carpal tunnel by inserting scissors through a transverse incision proximal to the carpal tunnel and dividing the ligament from the proximal to the distal end. When successful, this technique decompressed the median nerve without scarring the heel of the patient's hand, significantly decreased postoperative pain and morbidity.

Transverse incision and blind release have had the disadvantage of incomplete release of the carpal tunnel and occasional injury to the superficial arterial arch or the median nerve. The superficial palmar arterial arch lies just distal to the distal portion of the carpal ligament. The motor branch of the median nerve, which controls thumb opposition, is typically on the distal radial extent of the carpal tunnel, although anomalies can allow it to penetrate the carpal ligament in any of a number of positions and be subject to injury during blind release procedures.

Recently, arthroscopy has become one of the most rapidly developing techniques in orthopedic surgery. Arthroscopic meniscectomy has largely replaced conventional meniscectomy. Endoscopic approaches to carpal tunnel surgery have begun to be reported as satisfactory replacements for the open surgical procedures.

One such subcutaneous endoscopic procedure employs a clear plastic outer tube, or sheath, and a standard arthroscope. The tube has a bevel-shaped barrel about 100–175 mm in length and about 6 mm in diameter. The arthroscope is used in conjunction with a video-camera, recorder and light source.

A sterile skin marker is used to map the landmarks and establish the entry and exit portals. The proximal end of the pisiform bone is palpated on the volar surface of the wrist, and is circled with the marker. A line 1.0 cm in length is drawn radially from the circle. From the radial end of this line, another 1.0 cm line is drawn proximally. A third line is then drawn 1.0 cm radially from the proximal end of the second line. This marks the point of incision for the entry portal.

To identify the exit portal, the patient's thumb is placed in full abduction. A line is drawn across the palm from the distal border of the thumb to approximately the center of the palm. A second line is drawn from the web between the second and third fingers to meet the first line, forming a right angle. A line bisecting the right angle is extended approximately 1 cm proximal from the vertex to establish the incision point for the exit portal.

Following the incision of the wrist area, an obturator is inserted into the carpal tunnel from the radial side of the palmaris longus tendon to help guide insertion of the videoarthroscope. The obturator is then removed and the clear plastic tube inserted. The videoarthroscope is then advanced into the tube. The endoscope is removed and reinserted on the opposite side of the palmaris longus tendon. A series of progressive cuts are then made with three different specialized surgical knives inserted along the side of the clear plastic tube to cut the transverse carpal ligament. Three of the cuts are made with the arthroscope in the proximal opening while the knives are inserted in the distal opening and the remaining two cuts are made with the arthroscope in the distal opening while the knives are inserted in the proximal opening. The tube has a closed, generally rounded distal end and an open proximal end through which the videoarthroscope and/or a knife may be inserted. A slot is provided along a portion of its length through which the cutting edge of the knife projects to cut the desired site. It is believed that visualization may be distorted because of the curved clear wall of the tube.

The Agee Carpal Tunnel Release System, employs a videoscope, a disposable knife cone, a hand piece with a trigger, three curved obturators and one freer. The obturators are used consecutively to make a channel. The hand piece, which has an elongate shaft portion, is then inserted into the channel via the hook of hamate. When in the desired position, the trigger is pressed to activate a knife blade which pops up through a window in the elongate shaft. The hand piece is then drawn back to cut the ligament. The exposed blade cannot be viewed during the procedure. This device was withdrawn from the market.

Heel spur syndrome or pain is usually caused by a mechanical problem involving the structural alignment of the foot. There is a dense fibrous band of tissue in the bottom of the foot know as the plantar fascia which inserts into the heel bone and spreads out into the foot. Misalignment of the foot can exert excessive tension on this band of tissue causing inflammation and pain. The size or pressure of a heel spur does not always correlate with the amount of pain.

Conservative therapy is usually attempted first. This can consist of strappings, oral anti-inflammatory drugs, orthotic devices, etc. A high percentage of cases are successfully treated without surgery. However, in some cases, pain and discomfort continue after conservative methods have been exhausted. In such cases, surgery is recommended.

Traditional heel spur surgery involves making a large incision on the inside of the heel and dividing the plantar fascia ligament visually. This incision would then be sutured and the plantar fascia would heal and fill in with scar tissue. Thus the plantar fascia would become longer after surgery which would in turn relieve the tension on the ligament which was the cause of the pain.

Because of the large incision involved, traditional heel spur surgery resulted in the patient being unable to bear any weight on the heel for two to four weeks which prevented early return to work or recreational activities.

Alternatively, this procedure may be performed endoscopically using a revolutionary technique developed by Stephen L. Barrett D.P.M. and Stephen V. Day D.P.M. which significantly reduces trauma to the foot and speeds recovery. This procedure is the subject of a separate patent application now being pursued by Drs. Barrett and Day. Using the endoscopic technique, the patient can usually walk immediately after the procedure and is generally returned to a regular shoe within three days.

The endoscope division of the plantar fascia, or endoscopic plantar fasciotomy divides the plantar fascia endoscopically rather than using the traditional open technique in much the same way that the carpal tunnel ligament may be divided endoscopically rather than using the traditional open technique. The surgical instruments which are the subject of this patent application were also designed for and used for the plantar fasciotomy as well as the relief of carpal tunnel syndrome.

Chow U.S. Pat. No. 5,029,573 discloses an endoscopic method and instruments for relief of carpal tunnel syndrome.

Agee U.S. Pat. No. 4,962,770 discloses another endoscopic method and instruments for relief of carpal tunnel syndrome.

Wappler U.S. Pat. No. 1,880,551 shows a surgical endoscope.

Yoon U.S. Pat. No. 4,254,762 shows a safety surgical endoscope.

Santangelo U.S. Pat. No. 4,610,242 shows a surgical endoscope and surgical knife therein.

Storz U.S. Pat. No. 4,656,999 shows a surgical endoscope with surgical blade moved by a scissors type operator.

Ward U.S. Pat. No. 3,367,335 shows another surgical knife with replaceable blade.

Goodman U.S. Pat. No. 1,554,083 describes a surgical knife with replaceable blade.

Donovan U.S. Pat. No. 4,620,547 describes a reverse cutting surgical knife for electronic surgery.

Nicholson U.S. Pat. No. 4,497,320 describes another reverse cutting surgical knife for arthroscopic surgery.

Whipple U.S. Pat. No. 4,552,206 describes a scissors type surgical instrument for arthroscopic surgery.

Lichtman U.S. Pat. No. 286,438 shows a design for a surgical obturator.

Matwijcow U.S. Patent No. 187,320 shows a design for surgical scalpel handle.

SUMMARY OF THE INVENTION

One of the objects of this invention is to provide a new and improved assembly of surgical instruments for use in endoscopic surgical correction of carpal tunnel syndrome, heel spur syndrome and other surgical procedures requiring endoscopic tissue division.

Another object of this invention to provide a new and improved obturator and slotted cannula for guiding a new and improved single hooked surgical knife in an endoscopic procedure wherein the cannula is substantially smaller and shorter than those used heretofore reducing the trauma of operation substantially, and where the height of the knife is not as great so as to avoid unnecessary damage to surrounding tissue.

Another object of this invention to provide a new and improved obturator and slotted cannula for guiding a new and improved single hooked surgical knife in an endoscopic procedure wherein the obturator and knife handles are of an ergonometric construction.

Another object of this invention is to provide a new and improved obturator, slotted cannula and hooked surgical knife for use in an endoscopic surgical procedure wherein the knife handle has a curved grip which facilitates pulling the knife blade out of the cannula in performing the cutting procedure.

Another object of this invention is to provide a new and improved obturator and slotted cannula for guiding a single new and improved hooked surgical knife in an endoscopic surgical procedure wherein the obturator and cannula are constructed for ease of independent rotation.

Another object of this invention is to provide a new and improved surgical procedure for endoscopic surgical correction of carpal tunnel syndrome.

Another object of this invention is to provide a new and improved surgical method and instrument for carpal tunnel release which reduces postoperative pain and morbidity while minimizing the risk of injury to neural or vascular tissue surrounding the carpal ligament.

Another object of this invention is to provide new and improved surgical instruments for use in other procedures requiring endoscopic tissue division such as the plantar fasciotomy which instruments reduce postoperative pain and morbidity while minimizing the risk of injury to surrounding tissue.

Another object of this invention is to provide a new and improved endoscopic carpal tunnel release procedure and instruments for performing various endoscopic tissue division procedures which permit the direct, undistorted visualization of the incision site while the cut is being made.

Still another object of this invention is to provide a new and improved carpal tunnel release procedure and instruments for performing various endoscopic tissue division procedures which create a clearly defined unobstructed work space to enhance visualization and accuracy of the endoscopic procedure.

Still another object of this invention is to provide a new and improved surgical method and instruments which provides for the insertion of a single probe into a body cavity and the manipulation of selected tissue under continuous observation.

Still another object of this invention is to provide a new and improved position for the hand and wrist during an endoscopic carpal tunnel procedure to minimize the risk of fracture of the hamate and of pushing the cannula through the ligament instead of distal to it while aiding the surgeon in identifying the distal margin of the transverse carpal ligament.

Still another object of this invention is to provide a new and improved endoscopic carpal tunnel release procedure.

Still another object of this invention is to provide a new and improved endoscopic surgical procedure employing an obturator and slotted cannula for guiding a surgical knife to cut the carpal ligament.

Still another object of this invention to provide a new and improved endoscopic surgical procedure employing an obturator and slotted cannula for guiding a surgical knife to cut the carpal ligament and providing a viewing system on insertion of a videoarthroscope in the cannula, Another object of the invention is to provide a method of releasing the carpal tunnel ligament with a single new and improved hooked surgical knife and single cut, cutting the carpal ligament by means of the hooked knife in s slotted cannula without the need of additional knives or cuts, Still another object of this invention is to provide a new and improved endoscopic surgical procedure employing an obturator and slotted cannula for guiding a surgical knife to cut the carpal ligament wherein the cannula and obturator are substantially smaller and shorter than those used heretofore and the trauma of the operation is substantially less, Still another object of this invention is to provide a new and improved endoscopic surgical procedure employing an obturator and slotted cannula for guiding a surgical knife to cut the carpal ligament wherein the obturator and knife handles are of ergonometric construction.

Still another object of this invention is to provide a new and improved endoscopic surgical procedure employing an obturator and slotted cannula for guiding a surgical knife to cut the carpal ligament in a single cut wherein the knife has replaceable blades which reduce expenditure considerably, Still another object of this invention is to provide a new and improved endoscopic surgical procedure employing an obturator and slotted cannula for guiding a surgical knife to cut the carpal ligament wherein the knife handle has a curved grip which facilitates pulling the knife blade out of the cannula in performing the cutting procedure.

Still another object of this invention is to provide a new and improved endoscopic surgical procedure employing an obturator and slotted cannula for guiding a surgical knife to cut the carpal ligament wherein the obturator and cannula are constructed for ease of independent rotation.

Still another object of this invention is to provide a new and improved endoscopic surgical equipment employing an obturator and slotted cannula for guiding a surgical knife to divide the plantar fascia in treatment of heel spur syndrome.

A further object of the invention is to provide a method for dividing the carpal ligament under visual inspection during carpal tunnel release, while minimizing the risk of injury to surrounding tissue.

A further object of the invention is to provide a method for dividing the carpal ligament under visual inspection during carpal tunnel release, while minimizing the risk of injury to surrounding tissue, wherein an incision is made at both ends of the carpal tunnel and one probe comprising a cutting blade and another probe comprising an optical system is inserted therein, the blade being operated to divide the carpal ligament in a single cut, thereby releasing the carpal tunnel, while the optical system enables continuous observation of the portion of the cutting blade within its field-of-view.

A further object of the invention is to provide a custom surgical knife which may be manufactured economically for use with replaceable blades.

Other objects of the invention will become apparent from time to time throughout the specification and claims as hereinafter related.

These objects and other objects of the invention are accomplished by a novel apparatus for endoscopic surgical treatment of carpal tunnel syndrome, heel spur syndrome and endoscopic division of other tissues and a novel method for endoscopic treatment of carpal tunnel which include a slotted cannula, a cannula with a bridged slot, an obturator for guiding the cannula into a body opening, a carpal elevator, a plantar elevator, a retractor, a hooked surgical knife, a push surgical knife and triangular surgical knife, a probe and a rasp.

To determine the entrance portal, a surgical marking pen is used to place a mark approximately one centimeter long at the proximal wrist crease with radial border at the palmaris longus tendon. A scale is then placed along the midline of the ring finger in line with the palmaris longus tendon and two dots are marked up on the palm; one three centimeters and one four centimeters from the distal wrist crease. The entrance portal is made via an incision the length of the mark on the wrist, and the exit portal is made between the two dots on the palm. This marking procedure is faster, requires less measuring and marking and conceals the proximal wound scar better. The elevator and retractor are used in separating tissue at a surgical opening into the wrist or hand and the obturator and cannula are inserted into the opening for endoscopic release of the carpal ligament. The obturator is removed and a videoarthroscope is inserted in the distal end of the cannula while the knife is inserted in the proximal end to permit direct observation of the procedure as the ligament is divided in one step distally to proximally. The instruments are very small and leave only small openings which reduce the trauma and facilitate early recovery from the surgical procedure.

BRIEF DESCRIPTION OF THE DRAWINGS

FIG. 1 is a plan view of an obturator used in the surgical method of this invention.

FIG. 2 is a plan view of a slotted cannula used in the surgical method of this invention.

FIG. 3 is a view in left elevation of the cannula shown in FIG. 2;

FIG. 4 is a view in right elevation of the cannula shown in FIG. 2;

FIG. 5 is a plan view of the obturator assembled in the slotted cannula for use in the surgical method of this invention.

FIG. 6 is a view in elevation of the elevator used in the surgical method of this invention.

FIG. 6A is a plan view of the elevator of FIG. 6 used in the surgical method of this invention.

FIG. 7 is a view in elevation of the retractor used in the surgical method of this invention.

FIG. 7A is a plan view of the retractor of FIG. 7 used in the surgical method of this invention.

FIG. 8 is a view in elevation of a handle having openings at opposite ends for receiving elevator or retractor blades.

FIG. 9 is a view in elevation of the handle for the surgical knife used in the surgical method of this invention.

FIG. 9A is a left end view of the handle of FIG. 9 used in the surgical method of this invention.

FIG. 10 is a view in elevation of the blade for the surgical knife used in the surgical method of this invention.

FIG. 10A is a plan view of the blade of FIG. 10 used in the surgical method of this invention.

FIG. 11 is a view in elevation of the assembly of the handle of FIG. 9 and blade of FIG. 10.

FIG. 12 is an isometric view of a hand bent backward over a towel roll (the amount of bending being exaggerated) with two incisions therein for receiving the instruments of FIG. 1-11 for carpal tunnel surgery.

FIG. 18 is a plan view of a slotted cannula with bridges at both ends.

FIG. 19 is a left elevation of the cannula shown in FIG. 18.

FIG. 20 is a cross sectional elevation of an alternative embodiment of a handle for use with replaceable blades.

FIG. 21 is an isometric view of the handle of FIG. 20 with a blade in place.

FIG. 22 is a plan view of the bottom side of the handle and blade of FIG. 21.

FIG. 23 is an elevation of a pull blade for use with the handle of FIG. 20.

FIG. 24 is a plan view of the blade of FIG. 23.

FIG. 25 is an elevation detail for a pull blade.

FIG. 26 is a top plan view of FIG. 25.

FIG. 27 is an elevation detail of a triangle blade.

FIG. 28 is a top plan view of FIG. 27.

FIG. 29 is an elevation of a push blade.

FIG. 30 is a top plan view of FIG. 29.

FIG. 31 is an elevational view of an elevator for plantar fasciotomy.

FIG. 32 is a top plan view of the elevator of FIG. 31.

FIG. 33 is an elevational view of a rasp.

FIG. 34 is a top plan view of the rasp of FIG. 33.

FIG. 35 is a top plan view detail of the rasp head of the rasp of FIG. 34.

FIG. 36 is a detail top plan view of a probe.

FIG. 37 is an elevational view of the rasp head of FIG. 35.

FIG. 38 is an elevational view of the probe of FIG. 36.

DESCRIPTION OF THE PREFERRED EMBODIMENTS

The Surgical Instruments

Figure 13:
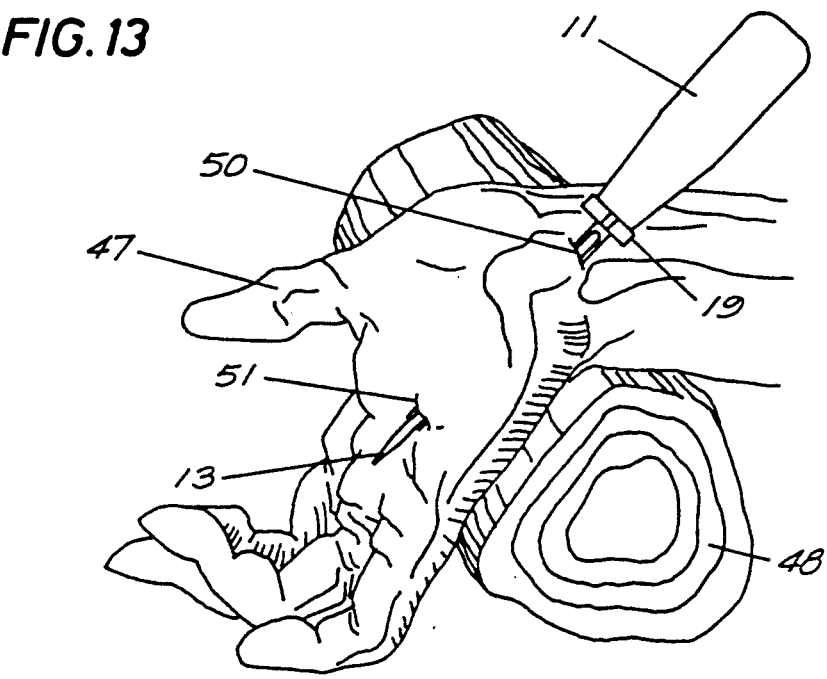
FIG. 13 is an isometric view of a hand bent backward over a towel roll (the amount of bending being exaggerated), as in FIG. 12, with an obturator/slotted cannula assembly inserted through the two incisions therein for carpal tunnel surgery.
Figure 14:
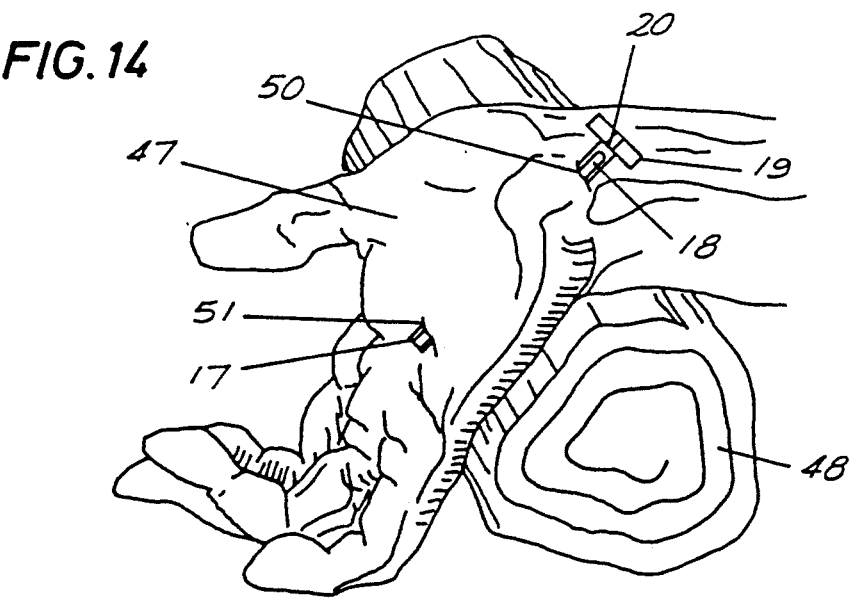
FIG. 14 is an isometric view of a hand bent backward over a towel roll (the amount of bending being exaggerated), as in FIG. 13, with the slotted cannula assembly inserted through the two incisions therein and the obturator removed for carpal tunnel surgery.
Figure 15:
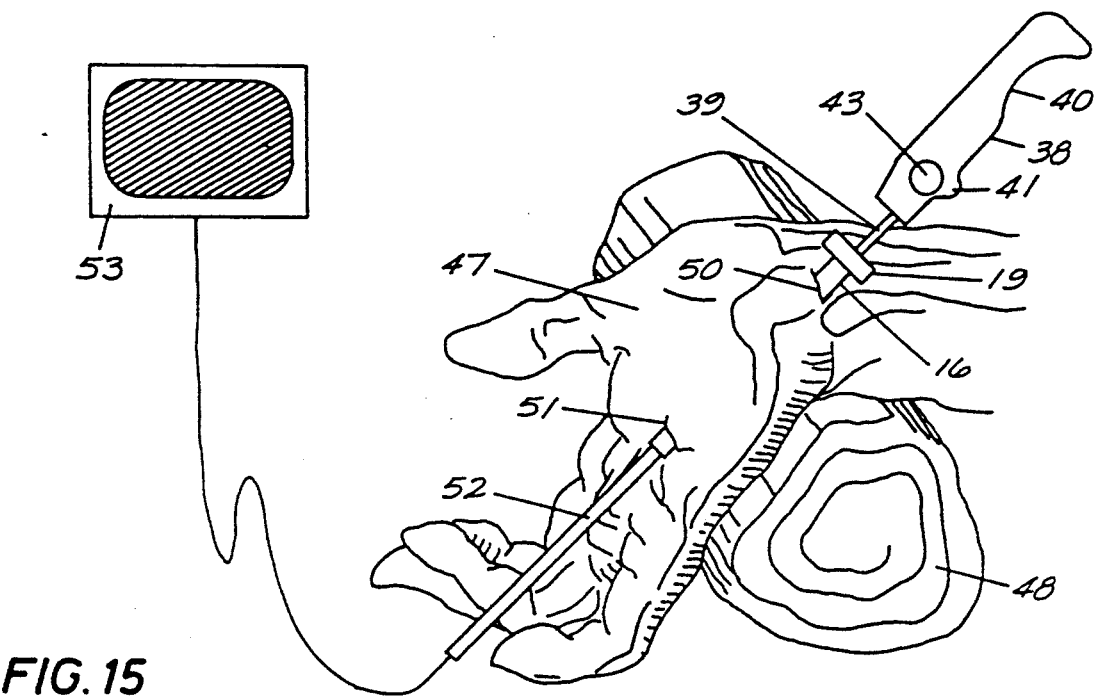
FIG. 15 is an isometric view of a hand bent backward over a towel roll (the amount of bending being exaggerated), as in FIG. 14, with the slotted cannula assembly inserted through the two incisions therein and the hooked surgical knife inserted from the proximal end and the videoarthroscope inserted from the distal end.

Referring to the drawings by numerals of reference, and more particularly to FIG. 1-11 and 18-30, there are shown the improved surgical instruments forming a preferred embodiment of this invention and used in the method of surgical correction of carpal tunnel syndrome as described hereinafter. FIG. 31 and 32 depict an instrument that is specially designed for endoscopic plantar fasciotomy procedures. In the description of these instruments, the materials of construction and dimensions are somewhat critical for obtaining the desired results and improved recoveries in endoscopic surgery.

An obturator 10, in FIG. 1, comprises a handle 11 and rod 12. Both parts are preferably formed of #303 surgical stainless steel. Handle 11 is about 3.370" long and an O.D. of C.975" at its larger end, tapering about 7° to a 0.600" diameter smaller end. The larger end has an edge curvature with a radius of 7/16". Rod 12 is 0.170" O.D. and has a smooth exterior surface which tapers to a distal rounded point 13. The base of rod 12 has 10/32" threads 14 which screw into a hole 15 in the end of handle drilled with a #21 drill and threaded with a 10/32" tap.

A slotted cannula 16, in FIG. 2-4, comprises a tube 17 with a slot 18 therein. Tube 17 is secured on collar 19 having a notch 20 aligned with slot 18. Both parts are preferably formed of #303 surgical stainless steel. Collar is 0.700" O.D. and 0.290" thick. The overall length of cannula 16 is 3.855". Tube 17 is 0.203" O.D. and 0.171" I.D. and slot 18 is 0.0990" wide.

An alternate of the slotted cannula 16A is shown in FIG. 18 and 19. The tube 17A is secured on collar 19A having a notch 20A which is aligned with the slot 18A. While the materials of construction and dimensions are generally the same as the slotted cannula 16 depicted in FIG. 2-4, the slot 18A at the end of the tube 17A opposite the collar 19A is bridged by a portion 17B of the tube and the end tapered to minimize tissue trauma during insertion.

When obturator 10 is assembled (as in FIG. 5) with rod 12 extending through cannula 16 or 16A it is free to rotate therein and rounded point 13 extends beyond the end of the cannula to facilitate insertion of the assembly into a body cavity. The obturator is not interlocked with the cannula and can be rotated within the cannula thereby reducing tissue trauma.

Elevator 21, in FIG. 6 and 6A, comprises a handle 22 and blade 23. Both parts are preferably formed of #303 surgical stainless steel. Handle 22 is knurled for accuracy in handling. Handle 22 is about 5.000" long has an O.D. of 0.250" with a slight taper. Handle 22 has ¼" deep hole 24 with internal threads 25 provided by a 10/31" tap. Blade member 23 is cylindrical at its rear end and tapers to end 26 having a rebent blade portion 27, 0.200" wide and 0.055" thick, with a dihedral angle of about 140°. Blade member is 2.275" long, 1.400" from the shoulder to the base of blade portion 27. The base of blade member 23 has 10/32" threads 28 which screw into hole 24 in the end of handle 22.

In FIG. 7 and 7A, a retractor 29 comprises a handle 22 (the same handle as elevator 21) and blade 30. Both parts are preferably formed of #303 surgical stainless steel. Handle 22 is knurled for accuracy in handling. Handle 22 is about 5.000" long has an O.D. of 0.250" with a slight taper. Handle 22 has a ¼" deep hole 24 with internal threads 25 provided by a 10/32" tap. Blade member 30 is cylindrical at its rear end, 1.950" in length, and tapers to end 31 having a hooked blade portion 32, 0.250" wide and 0.030" thick. The base of blade member 30 has 10/31" threads 33 which screw into hole 24 in the end of handle 22.

A double ended handle 33 is shown in FIG. 8 for carrying instruments at opposite ends. Handle 22 is knurled for accuracy in handling. Handle 33 is about 3.250" long has an O.D. of 0.250" with a slight taper. Handle 33 has ¼" deep holes 34 and 35 at opposite ends with internal threads 36 and 37 provided by a 10/32" tap. Holes 34 and 35 may receive the threaded ends of two different elevator blade members 23 or two different retractor blade members 31 or may support an elevator blade member at one end and a retractor blade member at the other end. Handle 33 is preferably formed of #303 surgical stainless steel and has a knurled handling surface.

In FIG. 33-35 and 37 are pictured a four prong rasp 330 which is useful when there is bone impingement into the carpal tunnel. The rasp comprises a handle 331 (which could be the same handle as 21) and blade 332, both of #304 surgical stainless steel. Handle 331 is knurled for accuracy in handling an is about 3.81 inches long and about ¼ in diameter. The blade 332 is 3.815 inches long and is tapered for the first 3.415 inches of its length from the handle. The prongs 333 have no sharp corners and are spaced about 0.10 inches apart. Each of the prongs has a 45° incline from the end of the blade toward the handle with a 0.025 flat inch top section leading to the vertical section. If desired the base of the blade member 332 could have male threads (not shown) which would mate with the female threads of the handle.

In FIG. 36 and 38 there is shown similar to rasp 330 and attached or attachable to an identical handle to 331 a probe blade 336 which is about 3.82 inches long having a 0.8° taper along its length away from the handle. The probe end 337 is perpendicular to the blade 336 and is 0.075 inches in diameter and 0.16 inches high.

FIG. 31 and 32 depict an elevator 310 which is useful in the plantar fasciotomy procedure discussed above. The handle 312 is essentially identical to handle 331. The elevator blade 311 is curved along its length as opposed to the blade 23 shown in FIG. 6 and 6A and used for the carpel tunnel procedure.

In FIG. 9 and 9A there is shown the handle 38 for a hooked surgical knife blade 39 (FIG. 10 and 10A). Handle 38 is 3.540" long, substantially rectangular with a curved (0.875" radius) edge 40 and projection 41 providing gripping surfaces for the surgeon's hand for accuracy of control of the instrument in use. Handle 38 has a longitudinal (0.080") slot 42 which blade 39 is secured by a set screw and knob 43. A suitable surgical knife blade 39 is secured by a set screw and knob 43. A suitable surgical knife blade 39 is 4.920" long (other sizes may be used). Knife blade is about 0.080" wide (fitting slot 42) and has thickness tapering from 0.145" at the end 44 fitting into slot 42 to 0.065" at the cutting end 45. The cutting end 45 is hook shaped, about 0.160" deep, and has a sharp cutting edge 46 inside the hook for cutting on backward movement. Handle 38 is preferably made of #330 surgical stainless steel. Blade 39 is preferably made of #440 surgical stainless steel heat treated to a hardness of 59–60 Rockwell C.

In FIG. 20-22 there is shown an alternate handle 38A for hooked surgical knife blade 39A, push blade 39B and triangular blade 39C (FIG. 23-30). The handle 38A is approximately 4.540 inches long, substantially rectangular with a curved edge 40A on the under side providing for a gripping surface for the surgeons's hand for accuracy of control of the instrument in use. The upper surface of handle 38A comprises a first substantially flat portion 207, a curved cut-away portion 202 and a second substantially flat portion 208. The first flat portion 207 includes a deep slot 42A in which is mounted locking member 201. Locking member 201 is rotatably secured in slot 42A by pin 203 and is biased upward at the distal end 210 by spring 205. Proximal end 209 of locking member 201 has an upper surface which is flush with first flat portion 201 when in its natural biased position. The lower surface 212 of the distal end 209 of locking member 210 is shaped to conform to the shape of the proximal end 231 (see also FIG. 23 and 24) of a blade to be inserted therein. The proximal end of locking member 201 extends into curved cut-away portion 22 of the handle with the lower surface of the distal end of locking member 201 tapered upward to allow the member to rock about pin 203. To insert a blade 39A-39C the distal end 210 of locking member is pressed downward and the proximal end 231 of the blade is inserted and the locking member released. The spring 205 biases the distal end of the locking member downward into locking engagement with the proximal end of the blade.

FIG. 23-30 show the various blades 39A-39C for use with the handle. The complete length is shown for the hooked blade 39A only in FIG. 23 and 24, the remaining figures depicting the blade ends only. Each of the blades is approximately 4.915 inches in total length with an insertion end 231 which is substantially rectangular in shape or about 0.144 inches by 1.045 inches by about 0.090 inches think. The sides of each blade are flat with the blade being about 0.090 inches thick. The insertion end includes a notch 204A for receiving the projection 204 of the locking member. The notch is located in the top surface about 0.61 inches from the end of the insertion end and is about 0.017 inches deep by about 0.125 inches long. The blade is tapered from about 0.125 inches at the insertion end to about 0.60 inches at the cutting end.

While only three types of replaceable blades are shown, the handle is capable of serving for any blade useful for this type of surgery.

COMPARISON OF ENDOSCOPIC CARPAL TUNNEL RELEASE TO OPEN PROCEDURE

A safe open carpal tunnel release with complete division of the transverse carpal ligament requires division of more superficial structures including skin, subcutaneous fat, subcutaneous nerve fibers within it, palmaris breves muscle, palmar fascia and often hypothenar and thenar muscle fibers. This inevitably results in wound tenderness and so-called pillar pain. This tenderness is thought to be due to several factors including injury to subcutaneous nerves and especially traction during hand motion which is transmitted to the healing scar tissues in the palmar fascia and hypothenar and thenar muscles. This tenderness prevents the patient from placing direct pressure on the wound and from performing gripping motions which in turn causes delay in returning to full activities for weeks, months or years. In some cases, this pain is permanent. Potential complications of open carpal tunnel release are numerous as previously described in the literature. Endoscopic carpal tunnel release minimizes morbidity by minimizing surgical trauma, avoiding injury to the structures superficial to the transverse carpal ligament.

MATERIAL AND METHODS

Prior to performing the procedure described herein in vivo, the surgeon had performed the procedure in twelve cadaver hands with subsequent dissection, showing no ulnar artery injury, no ulnar nerve injury, no median nerve injury, no common digital nerve injury. In all cadaver specimens there was complete division of the ligament. Technique evolved throughout the cadaver procedures to the technique described herein.

INDICATIONS

Prior to performing endoscopic carpal tunnel release described herein, all patients were diagnosed with carpal tunnel syndrome on the basis of symptoms and physical examination with confirmation in all cases by abnormal nerve conduction studies All patients failed conservative treatment with splinting and anti-inflammatories.

SURGICAL PROCEDURE FOR ENDOSCOPIC CARPAL TUNNEL RELEASE

All procedures (shown in FIG. 12-17) were performed under general or IV regional anesthesia. The hand 47 was placed on a towel roll 48 and bent back about 5°-20° as shown in FIG. 12 (the drawing being exaggerated). Two incisions 50 and 51 were made in the wrist and palm. A 1 cm skin incision 50 was marked out from the midline or palmaris longus ulnarward. This mark was located 0.5 cm to 1.5 cm proximal to the distal wrist crease taking care to place the incision in the proximal wrist crease for wound concealment. Another incision 51, 3 and 4 cm distal to the distal wrist crease were marked in line with the ring finger.

Subcutaneous fat was dissected bluntly avoiding injury to cutaneous nerves. Retractors 29 were placed by the assistant to expose the volar forearm fascia; and L-shaped flap of fascia was raised. The synovial elevator 21 was used to dissect the ulnar bursa and synovium from the dorsal site of the transverse carpal ligament. The cannula 16 with obturator 10 serves as a hamate finder.

The slotted cannula 16 with obturator 10 was passed beneath the transverse carpal ligament 54 (FIG. 16) with the operators's dominant hand, regardless of whether or not the left or right hand was being operated upon. An endoscope 52 with its video camera attachment 53 is then inserted into the distal end of cannula 16. The endoscope and video camera may be any suitable known videoarthroscope with a camera optically connected to it. At least one, and preferably two monitor screens are provided for viewing by the surgeon and the surgeon's assistant.

The operators's contralateral thumb was used to palpate the tip of the obturator 10 as it passed beneath the distal edge of the transverse carpal ligament 54. The assistant then extended the patient's fingers and the wrist 10 degrees but not into a hyperextended position, as this was found to place increased stress on the hook of the hamate and there was a tendency to lever the obturator 10 around the hamate.

Figure 16:
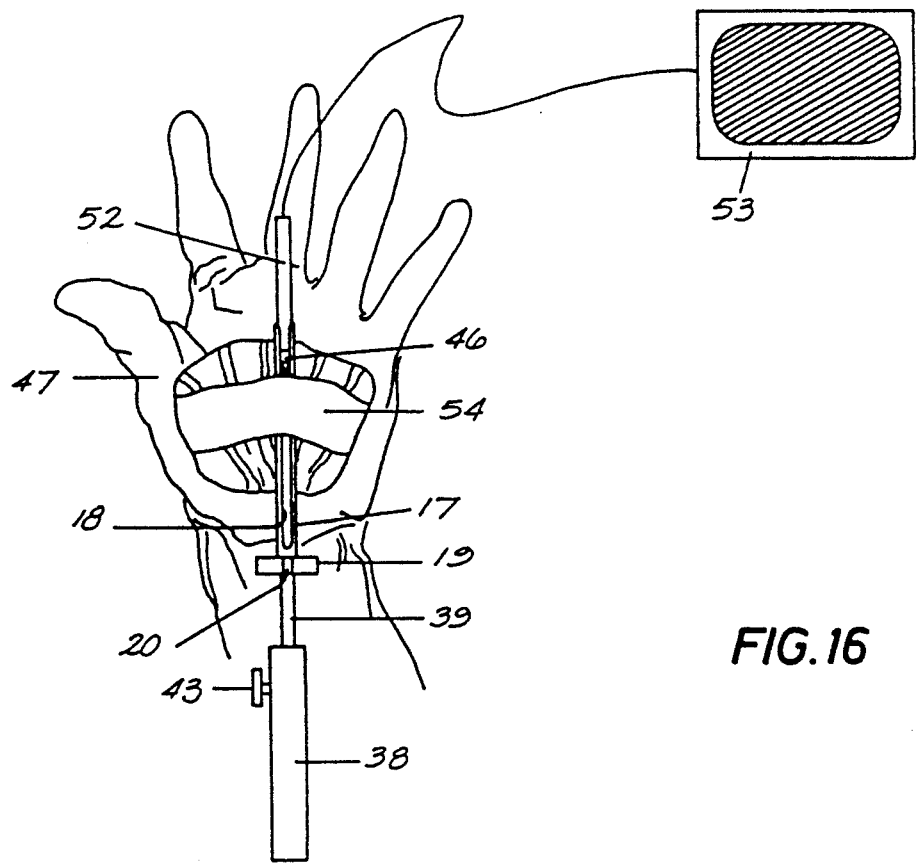
FIG. 16 is a plan view of a hand with the palm area broken away to show the location of the slotted cannula and hooked knife and the videoarthroscopic probe in relation to the carpal ligament.

The obturator tip 13 was palpated between the two distal skin marks and a 0.5 cm incision 51 was made. The obturator 10 and cannula 16 were then passed through the exit portal 51. The obturator 10 was removed and the assistant passed the endoscope 52 from distal to proximal ensuring a clear path. Then, with the endoscope 52 viewing the distal margin of transverse carpal ligament 54 on screen 53, a specially designed hooked scalpel 38, 39 was inserted into the proximal portion of the cannula 16 and then placed around the distal margin of the transverse carpal ligament 54 (FIG. 16).

Figure 17:
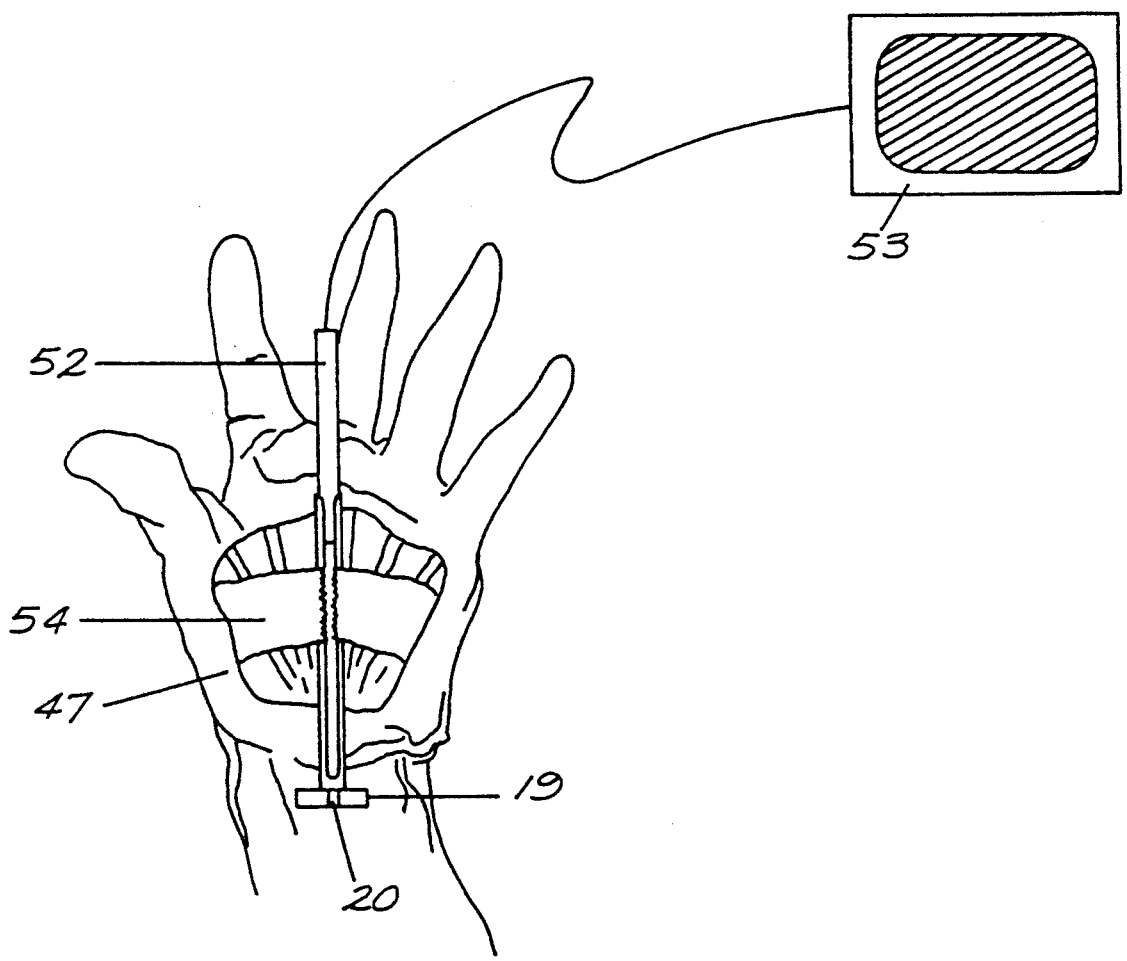
FIG. 17 is a plan view of a hand with the palm area broken away to show the location of the slotted cannula and the videoarthroscopic probe after operation of the knife to sever the carpal ligament.

The operator then withdrew the scalpel 38, 39 by pulling upon the hooked end of the handle as the assistant followed the cut moving the endoscope 52 from distal to proximal, thereby dividing the transverse carpal ligament 54 in one distal to proximal steady cutting motion (FIG. 17). The need for subsequent passes was rare. The transverse carpal ligament margins withdrew, allowing view (by endoscope 52 and screen 53) of the palmaris brevis, palmar fascia, and fat confirming complete division. A distal forearm fasciotomy was performed after removing the cannula 16. The wounds were closed, Bupivacaine instilled and tourniquet deflated. Pressure was held on the wounds for one to two minutes before applying the dressing and splint.

It is noted that the cannula and obturator are substantially smaller and shorter than those used heretofore and the trauma of operation is substantially less. The obturator and cannula are constructed for ease of independent rotation. The obturator and knife handles are of an ergonometric construction which facilitated handling. The knife handle has a curved grip which facilitates pulling the knife blade out of the cannula in performing the cutting procedure. These instruments used for carpal tunnel release reduce postoperative pain and morbidity while minimizing the risk of injury to neural or vascular tissue surrounding the carpal ligament. The surgical procedure releases the carpal tunnel with a single knife and single cut, cutting the carpal ligament by operation of a hooked knife in a slotted cannula without the need of additional knives or cuts or the need to remove the arthroscope from one end of the cannula and reinsert it in the other, thereby saving time and reducing trauma. This endoscopic surgical equipment is also effective to divide the plantar fascia in the treatment of heel spur syndrome.

POST OPERATIVE CARE

The patients were instructed to move their fingers post operatively but not to remove the splint or dressing. The dressing and splint were removed at ten days. The patients were then instructed in wound massage and allowed to resume normal activities when asymptomatic or minimally symptomatic with mild incisional pain.

EVALUATION OF TEST CASE RESULTS

The results of this new and improved endoscopic carpal tunnel release were evaluated on the basis of one hundred cases performed. The majority of the patients were asymptomatic at two weeks and returned to work at two weeks following surgery.

Complications in the group were less than 5%, and included persistent symptoms, mild reflex sympathetic dystrophy and transient paresthesia. The endoscopic carpal tunnel release technique described herein is believed to be the preferred technique and differs significantly from other techniques and instrumentation previously described.

The patients in the study were followed from one to ten months. The subjective finding of increased patient satisfaction (less pain, shorter recovery) particularly in patients who had previously undergone contralateral open carpal tunnel release cannot be quantified, however, this was quite obvious and it is felt to be one of the most important and convincing findings confirming the superiority of endoscopic carpal tunnel release over open carpal tunnel release.

The hypothesis that endoscopic carpal tunnel release is superior to open carpal tunnel release was upheld in Agee's report of the double-blind multicenter prospective randomized clinical study prior to release of the one portal system (presentation by John Agee, M.D. at the American Society for surgery of the Hand Annual Meeting in Toronto, Canada, 1990).

The studies made in developing this invention support the view that endoscopic carpal tunnel release should be offered as an option to all patients who are candidates for carpal tunnel release except those with concomitant nerve entrapment at Gyuon's canal or those who have bone impingement into the carpal tunnel or other abnormal pathology which is identified on the carpal tunnel view. The results to date suggest the incidence of anomalies, tumors, ganglions, or anomalous recurrent branch with ulnar sided exit is not significant to condemn all carpal tunnel syndrome sufferers to an open procedure with increased morbidity.

There is an acceptable low incidence of failed endoscopic carpal tunnel release attributable to (1) long-standing carpal tunnel syndrome with permanent nerve injury, 2) markedly thickened epineurium, 3) anomalies, 4) markedly proliferative tenosynovitis.

For the most part, diabetics responded as other patients did undergoing endoscopic carpal tunnel release. Whether or not diabetics with a non-concomitant diabetic neuropathy should have an open or endoscopic carpal tunnel release is yet unanswered.

This endoscopic procedure isolates the ligament from nerves and arteries prior to division with a technically easy maneuver as described. The obturator can easily be felt to pass beyond the edge of the transverse carpal ligament as the vibratory sensation is transmitted from the obturator tip passing along the fibrous ridges of the ligament to the operators hand holding the handle of the obturator. Once the ligament is isolated, it can easily and effectively be divided with one maneuver described herein which differs significantly from the five step process described by Chow.

Special instrumentation (FIG. 1–11) was specifically designed to accommodate this technique to minimize trauma to nerves and soft tissues. Occasional bruising and transient paresthesia were noted when using other two portal instrumentation systems.

While this invention has been described fully and completely, it should be understood that, within the scope of the appended claims, the invention may be practiced otherwise than as specifically described.

The invention claimed is:

1. An assembly of surgical instruments forming a kit for use in endoscopic surgical procedures comprising:
   a cannula comprising
   (i) a tube open at both ends,
   (ii) a cylindrical handle secured to the proximal end of said tube, and
   (iii) a longitudinal slot along said tube
   an obturator comprising
   (i) a cylindrical rod tapered at the distal end and adapted to fit in said tube,
   (ii) a handle secured to said rod at the proximal end; and
   a scalpel handle having two opposite handle sides defining a slot therebetween in the distal end of said scalpel handle for receiving a scalpel blade and having a biased locking member for securing said scalpel blade in said scalpel handle, a pivot member extending transversely through said biased locking member, said biased locking member being pivotable in a plane orthogonal to said pivot member and generally parallel to said two opposite handle sides, said slot being open along a top side of said scalpel handle for permitting pivoting of said locking member.

2. The assembly according to claim 1 wherein said locking member is rotatably mounted within said handle and biased such that the distal end is pressed downward in said handle, said locking member having a projection on the lower surface that is biased in a direction orthogonal to said pivot member and is adapted to engage a notch in an upper surface said scalpel blade;
  said scalpel handle having a hook shape finger groove along its lower side to allow an operator to have support when pulling a blade through said cannula.

3. The assembly of claim 1, further comprising:
  a bottom side interconnecting said two opposite handle sides and defining a bottom side of said slot opposite said top side, at least a portion of said locking member being movable into and out of an open portion of said slot along said top side of said scalpel handle, said bottom side providing an abutment surface for said scalpel blade, said locking member being rotatably biased to bias said scalpel blade in the direction of said abutment surface.

4. A scalpel handle, comprising:
  an elongate body having a lower edge with proximal and distal ends, said lower edge having a substantially arc-shaped finger grip contour adjacent a proximal end of said body and having an elongate base extending therefrom to said distal end;
  said body including two flange portions extending upwardly from said elongate base defining an elongate groove therebetween, said groove being open at the top of said body opposite said elongate base;
  an upper edge of said body opposite said lower edge having an arc-shaped locking member actuating groove, said arc-shaped locking member actuating groove defining the proximal side of said two flange portions such that said elongate groove opens into said arc-shaped locking member actuating groove;
  a locking member rotatably mounted in said elongate groove and extending past said proximal end of said two flange portions for pivotable movement in the locus of said arc-shaped locking member actuating groove and for pivotable movement into and outside of a portion of said open groove at said upper edge of said body;
  a pivot member extending through said locking member and connecting to each of said two flange portions, said locking member being thereby constrained to pivot parallel to said two flange portions and orthogonal to said pivot member;
  a biasing means disposed in said handle to bias the distal end of said locking member downward;
  a projection on the lower surface of said locking member of engagement with a notch on a scalpel blade.

5. A scalpel handle/scalpel combination comprising the scalpel handle of claim 4, and:
  a scalpel blade having a substantially rectangular shaft for insertion between and engagement with said two flange portions to prevent radial movement of said scalpel blade with respect to said scalpel handle, said scalpel having a notch along its upper surface to receive said projection and prevent distal-proximal movement of said scalpel blade with respect to said scalpel handle.

6. The scalpel handle according to claim 5 wherein said scalpel blade comprises a hook blade at the distal end.

7. The scalpel handle according to claim 5 wherein said scalpel blade comprises a push blade at the distal end.

8. The scalpel handle according to claim 5 wherein said scalpel blade comprises a triangular blade at the distal end.

9. A method of carpal ligament release comprising:
  making a first incision at a pre-selected site on a patient's wrist to establish an entry portal;
  inserting a cannula-obturator assembly into said entry portal, said cannula having a first and second end and a slot extending along its length, said obturator having an insertion end;
  passing said cannula-obturator assembly beneath the transverse carpal ligament such that said insertion end is at a point distal the distal edge of the carpal ligament and at a selected position beneath the palm of said patient, the fingers of said hand and the wrist being extended at an angle less than a hyperextended position;
  making a second incision in said palm in the locus of said selected position;
  passing the cannula-obturator assembly through said second incision;
  removing the obturator from the cannula;
  inserting an endoscope into the first end of said cannula;
  inserting an elongated cutting knife into the second end of said cannula, said cutting knife having a hook-shaped end defining an inner hook-shaped surface, a cutting edge being formed on said inner hook-shaped surface, said cutting edge facing said second end of said cannula, said hook-shaped end extending through said slot;
  moving said cutting knife distally from said second end until said inner hook-shaped surface hooks on the distal edge of said carpal ligament whereby said cutting edge engages the distal edge of said carpel ligament;
  moving said cutting knife proximally through said slot in said cannula to completely sever said carpal ligament in a single, distal-to-proximal movement;
  withdrawing said cutting knife from said cannula;
  withdrawing said endoscope from said cannula; and
  suturing said first and second incisions.

10. The method of claim 9, wherein said step of passing said cannula-obturator assembly beneath the transverse carpal ligament further comprises palpating said insertion end of said obturator as it passes beneath the distal edge of the transverse carpel ligament.

11. The method of claim 9, wherein said step of making a second incision includes palpating said insertion end of said obturator after said insertion end of said obturator passes beneath the distal edge of the transverse carpel ligament.

12. The method of claim 9, wherein the step of passing said cannula-obturator assembly beneath the transverse carpel ligament includes deflecting said patient's wrist backward about 5° to 20°.

13. The method of claim 9, wherein said step of making a first incision includes positioning said first incision approximately 0.5 to 1.5 centimeter proximal to the distal wrist crease in the proximal wrist crease from the palmaris longus and cutting ulnarward for approximately one centimeter.

14. The method of claim 9, wherein said step of inserting said cannula-obturator assembly beneath the transverse carpel ligament is made from the ulnar side of the palmaris longus.

* * * * *